United States Patent [19]

Onishi et al.

[11] Patent Number: 5,413,921
[45] Date of Patent: May 9, 1995

[54] METHOD OF THE PRODUCTION OF (S)-GAMMA-HALOGENATED-γ-HYDROX-YBUTYRIC ACID ESTERS

[75] Inventors: Norimasa Onishi; Megumi Shimaoka; Ikuo Kira; Masakazu Nakazawa, all of Kawasaki, Japan

[73] Assignee: Ajinomoto Co., Ltd., Tokyo, Japan

[21] Appl. No.: 66,239

[22] Filed: May 25, 1993

[30] Foreign Application Priority Data

May 28, 1992 [JP] Japan ................. 4-137111

[51] Int. Cl.$^6$ ................. C12P 7/62; C12P 41/00
[52] U.S. Cl. ................. 435/135; 435/280; 435/911; 435/940
[58] Field of Search ............ 435/280, 135, 141, 911, 435/940

[56] References Cited

U.S. PATENT DOCUMENTS 4,710,468 12/1987 Sih ................. 435/135
4,933,282 6/1990 Hasegawa et al. ................. 435/135

FOREIGN PATENT DOCUMENTS 61-146191 7/1986 Japan .
62-126997 6/1987 Japan .

OTHER PUBLICATIONS

Nakamura K., Tetrahed. Letts 25:3979–82 (1984).
Sih C, Ann NY Acad Sci 434:186–93 (1984).
Christen M, J. Chem Soc., Chem Commun 264–66 (1988).
Kataoka M, Arch. Biochem Biophys 294:469–74 (1992).
ATCC Catalogue of Yeasts 1990 pp. 92–93.

*Primary Examiner*—Marian C. Knode
*Assistant Examiner*—S. Saucier
*Attorney, Agent, or Firm*—Oblon, Spivak, McClelland, Maier & Neustadt

[57] ABSTRACT

The present invention provides a method of the production of (S)-γ-halogenated-β-hydroxybutyric acid esters at a high accumulation and a high yield. A microorganism belonging to the genus Stemphylium, Alternaria, Corynespora or Torulaspora is used to asymmetrically reduce a γ-halogenated-acetoacetic acid ester into an (S)-γ-halogenated-β-hydroxybutyric acid ester, and the (S)-γ-halogenated-β-hydroxybutyric acid ester produced is recovered from the reaction mixture.

21 Claims, No Drawings

METHOD OF THE PRODUCTION OF (S)-GAMMA-HALOGENATED-γ-HYDROXYBUTYRIC ACID ESTERS

DETAILED DESCRIPTION OF THE INVENTION

1. Field of the Invention

The present invention relates to a method of production of (S)-γ-halogenated-β-hydroxybutyric acid esters which are used in the synthesis of many types of pharmaceutical products.

2. Background of the Invention

Previous known methods of producing (S)-γ-halogenated-β-hydroxybutyric acid esters from γ-halogenated-acetoacetic acid esters which make use of the asymmetrical reducing capacity of microorganisms include a method which uses the unprocessed cells of the microorganisms belonging to the genus Saccharomyces, Pichia, Candida, Hansenula, Rhodotorula, Trichosporon, Cephalosporium, etc. (Bull. Chem. Soc. Jpn., Vol. 62, p.875, 1989; Annals New York Academy of Sciences, Vol. 434, p.186, 1984; Biotechnology letters, Vol. 12, p. 593, 1990). Further known methods include a method which uses an enzyme purified from cells of *Cellulomonas turbata* (Japanese Patent Application Laid-open No. 1-277494), and a method which uses an enzyme from a microorganism belonging to the genus Sporobolomyces, Fusarium, Verticilum, Pacecilomyces, etc. for asymmetrical reduction in which a diphase with water is formed (Appl. Environ. Microbiol., Vol. 56, p.2374, 1990; Japanese Patent Application Laid-open No. 63-309195).

However, methods which use unprocessed cells have disadvantages: oftentimes the optical purity of the product is lowered due to the by-product (R)-γ-halogenated-β-hydroxybutyric acid esters produced by other unnecessary reductases which are present in the microbial cells. Even when the optical purity of the product is high, inhibition of the metabolism and/or the growth of the cells occurs due to the presence of the starting material (γ-halogenated-acetoacetic acid ester) and the product ((S)-γ-halogenated-β-hydroxybutyric acid ester), and therefore the concentration of the starting material must be kept at a low level, making overall efficiency poor, or the metabolism of the cells is inhibited causing the cessation of the reaction prior to its potential completion point lowering the reaction yield.

Methods which conduct reduction in a diphase system using a purified enzyme solution and an organic solvent are excellent for obtaining high optical purities, high reaction yields and high concentrations of the accumulated product since they do not require the metabolism of a microorganism, but they are rendered industrially impractical by the fact that the coenzyme NADPH, which provides the reducing power to sustain the asymmetrical reduction reaction, must be constantly added to the reaction solution.

OBJECTS OF THE INVENTION

One object purpose of the present invention is to provide a novel, highly efficient and highly accumulative method of production of (S)-γ-halogenated-β-hydroxybutyric acid esters having a high degree of optical purity. Other objects will become clear upon a full reading of the disclosure.

BRIEF DESCRIPTION OF THE INVENTION

The inventors of the present invention have discovered that an (S)-γ-halogenated-β-hydroxybutyric acid ester may be obtained with a high degree of optical purity, in high yield and in high accumulation by subjecting a culture of at least one microorganism belonging to the genus Stemphylium, Alternaria, Corynespora or Torulaspora, or cells recovered from said culture, to a γ-halogenated-acetoacetic acid ester:

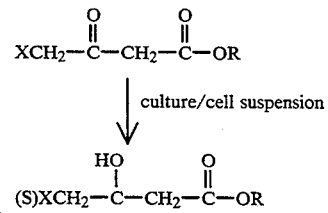

DETAILED DESCRIPTION OF THE INVENTION

The present invention provides a method of production of an (S)-γ-halogenated-β-hydroxybutyric acid esters which is characterized by subjecting a culture of a microorganism belonging to the genus Stemphylium, Alternaria, Corynespora or Torulaspora and capable of asymmetrically reducing a γ-halogenated- acetoacetic acid ester to an (S)-γ-halogenated-β-hydroxybutyric acid ester, or cells recovered from said culture, to an γ-halogenated-acetoacetic acid ester and recovering the (S)-γ-halogenated-β-hydroxybutyric acid ester produced thereby.

The microorganisms useful in the present invention include those belonging to the genus Stemphylium, Alternaria, Corynespora or Torulaspora which are capable of asymmetrically reducing a γ-halogenated- acetoacetic acid ester to an (S)-γ-halogenated-β-hydroxybutyric acid ester. Examples of such microorganisms are given below:

*Stemphylium astragali* IFO 7304
*Stemphylium loti* IFO 7299
*Stemphylium sarciniforme* IFO 7243
*Stemphylium trifolii* IFO 7300
*Alternaria steviae* IFO 31182
*Alternaria solani* IFO 7516
*Alternaria kikuchiana* IFO 7515
*Alternaria mali* IFO 8984 (ATCC 44899)
*Alternaria maritima* IFO 8618
*Alternaria porri* IFO 9762
*Alternaria bataticola* IFO 6187 (CBS 531.63)
*Corynespora cassiicola* IFO 7415 (*Corynespora vignicola* ATCC 42584)
*Corynespora cassiicola* IFO 7416
*Corynespora cassiicola* IFO 7484
*Corynespora cassiicola* IFO 30505
*Corynespora cassiicola* IFO 30507
*Corynespora sesameum* IFO 7485 (ATCC 42583)
*Torulaspora delbrueckii* IFO 704 (CBS 158)
*Torulaspora delbrueckii* IFO 1179 (CBS 1150)
*Torulaspora delbrueckii* IFO 1959 (CBS 813)

These microorganisms may be used whether they are wild strains, mutant strains thereof, or recombinant strains induced by a genetic method such as cell fusion, gene manipulation, etc. Further they may be used alone or in combination.

The culture medium used to obtain the culture of the above mentioned microorganisms is not particularly limited as long as the microorganism can grow in it. For example, any conventionally used medium containing carbon sources, nitrogen sources, inorganic salts, organic nutrients, etc. may be used to culture the microorganisms and such media are known in the art.

The carbon sources may be any which are utilized by the above mentioned microorganisms, and concrete examples thereof include sugars such as glucose, fructose, sucrose, dextrin, etc; alcohols such as sorbitol, ethanol, glycerol, etc.; organic acids such as fumaric acid, citric acid, acetic acid, propionic acid, etc., or their salts; hydrocarbons such as paraffin, etc.; or a mixture thereof.

The nitrogen sources available for use in the invention process include, for example, inorganic ammonium salts such as ammonium sulfate, ammonium chloride, etc.; ammonium salts of organic acids such as ammonium fumarate, ammonium citrate, etc.; nitrates such as sodium nitrate, potassium nitrate, etc.; organic nitrogen compounds such as peptone, yeast extract, beef extract, corn steep liquor, etc.; and mixtures thereof.

In addition, nutritive sources normally used for conventional culturing, such as inorganic salts, trace metals, vitamins, etc. may be mixed therewith in appropriate amounts. Also, a factor which promotes the growth of the microorganism, a factor which increases the capability of the production of the compound of interest according to the present invention, or a substance which effectively maintains the pH of the culture, may be added thereto as necessary. Examples of such compounds include phosphates, magnesium, iron, manganese, potassium, biotin and thiamine.

Cultivation is preferably effected while maintaining the pH of the culture solution at between pH 3.0 and pH 9.5, and more preferably at between pH 4 and pH 8. The temperature may be maintained at between 20° C. and 45° C., preferably 25° C. and 37° C., under aerobic or anaerobic conditions for about 1–8 days, and preferably 2–5 days. Conditions may be optimized by, e.g., using conditions which optimize the growth of the microorganism.

Examples of methods of subjecting said microorganism to the γ-halogenated-acetoacetic acid ester include a method in which a γ-halogenated-acetoacetic acid ester is added to and reacted with the microorganism culture, and a method in which the cells are recovered from the culture by means of filtration, centrifugation, etc. and resuspended in a buffer solution, water, etc., directly or after being washed, and then a γ-halogenated-acetoacetic acid ester is added thereto and reacted therewith. Here, it is sometimes advantageous to add a carbon source such as glucose, fructose, sucrose, etc. as a source of energy.

The γ-halogenated-acetoacetic acid ester may be added to the culture or the cell suspension as it is, being dissolved in water or an organic solvent which does not affect the reaction, or being dispersed in a surfactant, etc. It can be added in the whole quantity from the start of the reaction or in divided portions during the reaction. The concentration at which it is added is not particularly limited, but is preferably between about 0.1% and 10% by weight of the entire weight of the reaction media including starting materials, nutrients, etc.

The reaction is conducted within a pH range of between 3 and 9, and preferably between 5 and 8, and a reaction temperature range of between 10° C. and 60° C., and preferably 20° C. and 40° C., for a period of between about 1 and 120 hours, while stirring or allowed to stand.

Examples of γ-halogenated-acetoacetic acid esters which may be used as substrates according to the present invention include methyl γ-chloro-acetoacetate, ethyl γ-chloro-acetoacetate, ethyl γ-bromo-acetoacetate, etc., where the ester group is a straight or branched $C_1$–$C_6$ group and the halogen atom is selected from F, Cl, Br and I. These compounds are known and are described in, e.g., Tetrahedron Letters, Vol. 26, p. 4213, 1985; Tetrahedron Letters, Vol 26, p. 101, 1985; J. Am. Chem. Soc., Vol. 105, p. 5925, 1983, incorporated herein by reference. These compounds are each asymmetrically reduced by the action of the above-described microorganism to their corresponding (S)-γ-halogenated-β-hydroxybutyric acid esters. The (S)-γ-halogenated-β-hydroxybutyric acid esters thus produced have a high optical purity and are obtained at a high reaction yield, and may therefore be easily collected directly from the reaction solution or after removing the cells, using any known method of purification such as extraction with an organic solvent, distillation, column chromatography, etc. The products are useful for producing pharmaceutical products like (S)-Carnitine, Compactin, Mevinolin, etc. described in Tetrahedron Letters, Vol. 26, p. 101, 1985; J. Am. Chem. Soc., Vol. 105, p. 593, 1983; Tetrahedron Letters, Vol. 24, P. 1811, 1983; Tetrahedron Letters, Vol 26, p. 2951, 1985, incorporated herein by reference.

Having generally described this invention, a further understanding can be obtained by reference to certain specific examples which are provided herein for purposes of illustration only and are not intended to be limiting unless otherwise specified.

EXAMPLES

A more detailed description of the present invention is given below, with reference to the Examples. The analysis of the absolute configuration and the optical purity of the γ-halogenated-β-hydroxybutyric acid esters produced was made in the following manner: ten milliliters of ethyl acetate was added to 4.5 ml of a reaction mixture to extract any (S)-γ-halogenated-β-hydroxybutyric acid ester, which was then concentrated and dissolved in 1 ml of toluene, after which 10 mg of 3,5-dinitrophenylisocyanate and 0.1 ml of pyridine were added thereto. The resulting mixture was heated at 60° C. for one hour to produce a derivative, which was then diluted with ethanol and subjected to high performance liquid chromatography (hereunder abbreviated to HPLC) (Column: chiral cell OB for optical resolution, product of DAICEL CHEMICAL INDUSTRIES LTD.; Eluent: hexane:chloroform:2-propanol=10:3:2; Flow rate=0.7 ml/min).

Also, measurement of the reaction yield was effected by diluting the reaction solution with ethanol and subjecting it to HPLC (Column: Reverse phase YMC Pack A-312; Eluent: acetonitrile:water=4:6; Flow rate=1.0 ml/min).

Example 1

Five milliliters of a culture medium with the composition listed in Table 1 was poured into each test tube and sterilized with steam, and then one platinum loopful of cells of each of the microorganisms listed in Table 2 which had been previously obtained by culturing on a malt extract agar medium at 30° C. for 3 days were inoculated into the medium, and cultivation was effected at 30° C. for 2 to 4 days. Next, 50 mg of ethyl γ-chloro-acetoacetate and 25 mg of glucose were added to the culture, and the reaction was carried out by continuing the cultivation for another 24 hours. After completion of the reaction, an analysis was made of the absolute configuration and the optical purity of the ethyl γ-chloro-β-hydroxybutyrate produced thereby, and the amount of the product was measured to determine the reaction yield. The results are shown in Table 2.

TABLE 1

| Ingredient | Concentration |
| --- | --- |
| Glucose | 2.0 g/dl |
| Yeast extract | 1.0 g/dl |
| Polypeptone | 1.0 g/dl |
| $(NH_4)_2SO_4$ | 0.5 g/dl |
| $K_2HPO_4$ | 0.3 g/dl |
| $KH_2PO_4$ | 0.1 g/dl |
| $MgSO_4.7H_2O$ | 0.05 g/dl |
| $FeSO_4.7H_2O$ | 0.001 g/dl |
| $MnSO_4.4H_2O$ | 0.001 g/dl |
| pH 7.0 | |

TABLE 2

| Microorganisms | Absolute Configuration | Optical Purity (% e.e) | Reaction Yield (%) |
| --- | --- | --- | --- |
| Stemphylium astragali IFO 7304 | S | 99 | 94.2 |
| Stemphylium loti IFO 7299 | S | 94 | 92.4 |
| Stemphylium sarciniforme IFO 7243 | S | 99 | 87.4 |
| Stemphylium trifolii IFO 7300 | S | 99 | 86.2 |
| Alternaria steviae IFO 31182 | S | 99 | 98.2 |
| Alternaria solani IFO 7516 | S | 99 | 98.5 |
| Alternaria kikuchiana IFO 7515 | S | 99 | 94.0 |
| Alternaria mali IFO 8984 | S | 99 | 91.5 |
| Alternaria maritima IFO 8618 | S | 99 | 90.8 |
| Alternaria porri IFO 9762 | S | 99 | 90.2 |
| Alternaria bataticola IFO 6187 | S | 99 | 89.5 |
| Corynespora cassiicola IFO 7415 | S | 99 | 86.5 |
| Corynespora cassiicola IFO 7416 | S | 99 | 92.4 |
| Corynespora cassiicola IFO 7484 | S | 96 | 89.0 |
| Corynespora cassiicola IFO 30505 | S | 97 | 86.4 |
| Corynespora cassiicola IFO 30507 | S | 98 | 84.5 |
| Corynespora sesameum IFO 7485 | S | 99 | 85.0 |
| Torulospora delbrueckii IFO 704 | S | 95 | 80.5 |
| Torulaspora delbrueckii IFO 1179 | S | 92 | 82.6 |
| Torulaspora delbrueckii IFO 1959 | S | 94 | 84.6 |

Example 2

One platinum loopful of cells of *Alternaria solani* IFO 7516 were inoculated into a 500 ml Sakaguchi flask into which had been placed 50 ml of the culture medium described in Example 1, and shaking cultivation was effected at 30° C. for 4 days. After completion of the cultivation, the cells were collected by filtration and washed with an amount of a 50 mM phosphate buffer solution (pH 7.0) equal to that of the culture solution, and then suspended in 50 ml of the same buffer solution. To the resulting suspension were added 0.5 g of ethyl γ-chloro-acetoacetate and 0.5 g of glucose, and the reaction was effected while shaking at 30° C. for 12 hours. After completion of the reaction, the absolute configuration, optical purity and reaction yield of the ethyl γ-chloro-β-hydroxybutyrate produced thereby were measured by HPLC, which resulted in an (S)-form absolute configuration, an optical purity of 97%, and a reaction yield of 98.3%. Also, after completion of the reaction, the filtered, cell-free reaction solution was extracted 3 times using 50 ml of ethyl acetate and concentrated to obtain 476 mg of a crude ethyl γ-chloro-β-hydroxybutyrate (83% purity).

Example 3

The reaction was conducted in the same manner as in Example 2, but using ethyl γ-bromo-acetoacetate as the substrate. After completion of the reaction, the absolute configuration, the optical purity and the reaction yield of the ethyl γ-bromo-β-hydroxybutyrate produced thereby were measured by HPLC, and the results were an (S)-form absolute configuration, an optical purity of 95% and a reaction yield of 87.4%.

While the present invention has been described in terms of its specific embodiments, certain modifications and equivalents will be apparent to those skilled in the art and are intended to be included within the scope of the present invention, which is to be limited only by scope of the appended claims.

Example 4

The reaction was conducted in the same manner as in Example 2, but using methyl γ-chloro-acetoacetate as the substrate. After completion of the reaction, the absolute configuration, optical purity and reaction yield of the methyl γ-chloro-β-hydroxybutyrate produced thereby were measured by HPLC, and the results were an (S)-form absolute configuration, an optical purity of 92% and a reaction yield of 82.4%.

What is claimed as new and desired to be secured by Letters Patent of the U.S. is:

1. A method of producing (S)-γ-halogenated-β-hydroxybutyric acid esters, comprising the steps of:
    subjecting a γ-halogenated-acetoacetic acid ester to a culture of at least one microorganism selected from the group consisting of Stemphlium astragali, Stemphylium loti, Stemphylium sarciniforme, Stemphylium trifolii, Alternaria steviae, Alternaria solani, Alternaria kikuchiana, Alternaria mali, Alternaria maritima, Alternaria porri, Alternaria bataticola, Corynespora cassiicola, and Corynespora sesameum, and capable of asymmetrically reducing said γ-halogenated-acetoacetic acid ester to an (S)-γ-halogenated-β-hydroxybutyric acid ester, or to cells recovered from said culture in order to reduce said γ-halogenated-acetoacetic acid ester to the (S)-γ-halogenated-β-hydroxybutyric acid ester; and
    recovering said (S)-γ-halogenated-β-hydroxybutyric acid ester.

2. The method of claim 1, wherein said at least one microorganism is selected from the group consisting of Stemphylium astragali IFO 7304

*Stemphylium loti* IFO 7299
*Stemphylium sarciniforme* IFO 7243
*Stemphylium trifolii* IFO 7300
*Alternaria steviae* IFO 31182
*Alternaria solani* IFO 7516
*Alternaria kikuchiana* IFO 7515
*Alternaria mali* IFO 8984
*Alternaria maritima* IFO 8618
*Alternaria porri* IFO 9762
*Alternaria bataticola* IFO 6187
*Corynespora cassiicola* IFO 7415
*Corynespora cassiicola* IFO 7416
*Corynespora cassiicola* IFO 7484
*Corynespora cassiicola* IFO 30505
*Corynespora cassiicola* IFO 30507
*Corynespora sesameum* IFO 7485
*Torulaspora delbrueckii* IFO 704
*Torulaspora delbrueckii* IFO 1179 and
*Torulaspora delbrueckii* IFO 1959.

3. The method of claim 2, wherein said (S)-γ-halogenated-acetoacetic acid ester is a straight or branched $C_1$–$C_6$ ester.

4. The method of claim 1, wherein said (S)-γ-halogenated-acetoacetic acid ester is a straight or branched $C_1$–$C_6$ ester.

5. The method according to claim 1, wherein said microorganism is *Stemphylium astragali*.

6. The method according to claim 1, wherein said microorganism is *Stemphylium loti*.

7. The method according to claim 1, wherein said microorganism is *Stemphylium sarciniforme*.

8. The method according to claim 1, wherein said microorganism is *Stemphylium trifolii*.

9. The method according to claim 1, wherein said microorganism is *Alternaria steviae*.

10. The method according to claim 1, wherein said microorganism is Alternaria solani.

11. The method according to claim 1, wherein said microorganism is *Alternaria kikuchiana*.

12. The method according to claim 1, wherein said microorganism is *Alternaria mali*.

13. The method according to claim 1, wherein said microorganism is *Alternaria maritima*.

14. The method according to claim 1, wherein said microorganism is *Alternaria porri*.

15. The method according to claim 1, wherein said microorganism is *Alternaria bataticola*.

16. The method according to claim 1, wherein said microorganism is *Corynespora cassiicola*.

17. The method according to claim 1, wherein said microorganism is *Corynespora sesameum*.

18. A method of producing (S)-γ-halogenated-β-hydroxybutyric acid esters, comprising the steps of:
subjecting a γ-halogenated-acetoacetic acid ester to a culture of at least one microorganism selected from the group consisting of *Torulaspora delbrueckii* IFO 704, *Torulaspora delbrueckii* IFO 1179 and *Torulaspora delbrueckii* IFO 1959 and capable of asymmetrically reducing said γ-halogenated-acetoacetic acid ester to an (S)-γ-halogenated-β-hydroxybutyric acid ester, or to cells recovered from said culture in order to reduce said γ-halogenated-acetoacetic acid ester to the (S)-γ-halogenated-β-hydroxybutyric acid ester; and
recovering said (S)-γ-halogenated-β-hydroxybutyric acid ester.

19. The method according to claim 18, wherein said microorganism is *Torulaspora delbrueckii* IFO 704.

20. The method according to claim 18, wherein said microorganism is Torulaspora delbrueckii IFO 1179.

21. The method according to claim 18, wherein said microorganism is *Torulaspora delbrueckii* IFO 1959.

* * * * *

UNITED STATES PATENT AND TRADEMARK OFFICE
CERTIFICATE OF CORRECTION

PATENT NO. : 5,413,921
DATED : May 9, 1995
INVENTOR(S) : Norimasa ONISHI, et al.

It is certified that error appears in the above-indentified patent and that said Letters Patent is hereby corrected as shown below:

On the title page, Item [54] and Column 1, Lines 2-4, the title should read:

--METHOD OF THE PRODUCTION OF (S)-GAMMA-HALOGENATED-BETA-HYDROXYBUTYRIC ACID ESTERS--

Signed and Sealed this

Fifteenth Day of August, 1995

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,413,921
DATED : May 9, 1995
INVENTOR(S) : Norimasa ONISHI, et al.

It is certified that error appears in the above-indentified patent and that said Letters Patent is hereby corrected as shown below:

On the title page, Item [54] and Column 1, Lines 2-4, the title should read:

--METHOD OF THE PRODUCTION OF (S)-GAMMA-HALOGENATED-BETA-HYDROXYBUTYRIC ACID ESTERS--

Signed and Sealed this

Nineteenth Day of September, 1995

Attest:

BRUCE LEHMAN

Attesting Officer

Commissioner of Patents and Trademarks